United States Patent [19]
Ellis et al.

[11] Patent Number: 4,752,588
[45] Date of Patent: Jun. 21, 1988

[54] LUMINESCENT CHEMICAL SENSOR FOR GASES

[75] Inventors: Arthur B. Ellis; Gerald J. Meyer, both of Madison; George C. Lisensky, Beloit, all of Wis.

[73] Assignee: Minnesota Mining and Manufacturing Company, St. Paul, Minn.

[21] Appl. No.: 32,300

[22] Filed: Mar. 30, 1987

[51] Int. Cl.⁴ .......................................... G01N 27/12
[52] U.S. Cl. ............................. 436/172; 250/361 R; 73/23; 422/86; 422/88; 422/91; 436/164
[58] Field of Search .................... 356/445; 422/86, 88, 422/91, 98; 436/84, 164, 167, 172; 250/361 R

[56] References Cited
U.S. PATENT DOCUMENTS
4,645,932  2/1987  Ellis et al. .................... 250/361 R Primary Examiner—Barry S. Richman
Assistant Examiner—Michael S. Gzybowski
Attorney, Agent, or Firm—Donald M. Sell; James A. Smith; Mark A. Litman

[57] ABSTRACT

The presence of certain chemicals on the emitting surface of the surface-derivatized photoluminescent semiconductor alters the characteristics of radiation emitted from said surface. This alteration is used to indicate the presence of those chemicals in the environment.

20 Claims, 1 Drawing Sheet

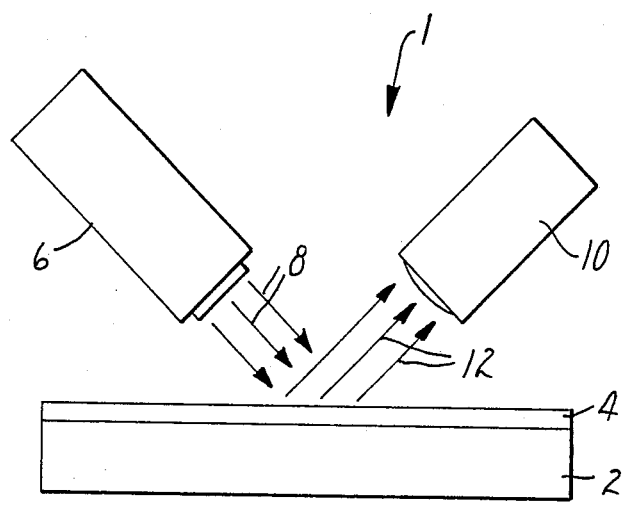

4,752,588

LUMINESCENT CHEMICAL SENSOR FOR GASES

TECHNICAL FIELD

The present invention relates to optically-coupled chemical sensing devices and to processes for detecting the presence of certain classes of chemical compounds.

BACKGROUND OF THE ART

Electroluminescence occurs in semiconductor materials that are capable of emitting visible or near visible radiation when an electrical current passes through the semiconductor. Photoluminescence can also occur in these materials. If external light is used to excite the semiconductor, a characteristic wavelength of light is emitted. These characteristic wavelengths vary amongst different photoluminescent semiconductors and can be varied in a single semiconductor by doping or changing the composition of the material.

Amongst the various studies on the luminescence of photostimulated or electroluminescent materials is "Luminescent Photoelectrochemical Cells", Streckert, H. H., Tong, J., and Ellis, A. B., *J. Am. Chem. Soc.*, Vol. 104, No. 2, 1982, pp. 581–588. It is noted therein that the intensity of light emitted by electroluminescence and photoluminescence varies directly with the applied voltage. The efficiency of charge transfer and good electrical contact at the surface is also noted as important in the efficiency of the process.

U.S. patent application Ser. No. 480,471, filed on Mar. 30, 1983, discloses semiconductor electrodes having multicolor luminescence. These semiconductors comprise solid-state solutions of three elements that vary in a vertically anisotropic manner. The preferred solid-state solutions are of cadmium, sulfur and selenium.

U.S. Pat. No. 4,211,586 discloses a method of forming a multicolor light-emitting array of diodes. The diodes are formed by differentially etching a graded n-type semiconductor and diffusing a p-type dopant into the surface of the n-type semiconductor to form a p-n junction diode.

U.S. Pat. No. 4,645,932 discloses an apparatus for detecting the presence of certain chemical compounds comprising a photoluminescent semiconductor having a metal coating on a radiation-emitting surface of the semiconductor, a source of actinic radiation that can impinge on the radiation-emitting surface of the semiconductor, and a means for detecting changes in the characteristics of radiation emitted from said radiation-emitting surface. The absorption of hydrogen into the metal layer is suggested as varying the height of the Schottky barrier of the diode and causing a change in spectral characteristics of the radiation emitted.

U.S. patent application Ser. No. 811,511, filed Dec. 20, 1985, describes an optically-coupled sensing apparatus of a photoluminescent semiconductor, a source of actinic radiation that can impinge on a radiation-emitting surface of the semiconductor, and a means for detecting changes in the characteristics of the radiation emitted from the radiation-emitting surface. The radiation-emitting surface has reacted thereon a compound capable of undergoing oxidation and/or reduction, the redox product of which reacted compound has a vertical charge distribution therein with respect to the radiation-emitting surface.

SUMMARY OF THE INVENTION

The present invention describes an optically-coupled sensing apparatus of a photoluminescent semiconductor, a source of actinic radiation that can impinge on a radiation-emitting surface of the semiconductor, and a means for detecting changes in the characteristics of the radiation emitted from the radiation-emitting surface. The radiation-emitting surface as by having reacted thereon a compound is capable of bonding to certain gases, undergoing oxidative addition and/or reductive elimination reactions, resulting in a change in the vertical charge distribution with respect to the radiation-emitting surface.

BRIEF DESCRIPTION OF THE DRAWING

Figure shows a schematic representation of the sensing apparatus of the present invention.

DETAILED DESCRIPTION OF THE DRAWING

The FIGURE shows a schematic representation of the sensing device (1) of the present invention. The photoluminescent semiconductor layer (2) has a surface layer (4) capable of bonding to certain gases, such as a surface having bonded thereto a compound capable of undergoing further oxidative addition or reductive elimination reacted onto the surface of the semiconductor layer (2). A source (6) of actinic radiation (8) is provided to direct radiation (8) at the semiconductor layer (2). A detector (10) is provided to detect changes in the radiation (12) emitted from the semiconductor layer (2).

DETAILED DESCRIPTION OF THE INVENTION

The present invention uses the modification of electric fields in compounds on the surface of photoluminescent semiconductors to alter or modulate the electric field of the semiconductor. The modulation of the electric field alters the photoluminescence of the semiconductor, and this alteration can be detected by sensing means.

A compound can be coated or preferably reacted onto the surface of the semiconductor. The coated material or reacted compound must be capable of an oxidative addition or reductive elimination reaction. Such reactions are well known in organometallic chemistry and are illustrated below for a specific compound, Vaska's complex.

The reactive surface of the semiconductor can be obtained by chemical or photoelectrochemical (PEC) etching; PEC etching is described in Streckert, H. H., Tong, J., and Ellis, A. B., *J. Am. Chem. Soc.*, Vol. 104, No. 2, 1982, pp. 581–588. Reactivity is measured by the ability to engage in chemical bonding to gaseous compounds. Preferred forms of bonding include adduct formation and hydrogen bonding.

Adduct formation involves complexation of a Lewis acid with a Lewis base. Such reactions are described in J. E. Huheey, *Inorganic Chemistry*, 3rd ed., Harper and Row: New York (1983), Chapter 7. Sites of Lewis basicity on the semiconductor surface include phosphorus, arsenic, oxygen, sulfur, or selenium atoms and these can interact with gaseous Lewis acid molecules like sulfur dioxide and boron trifluoride. Sites of Lewis acidity on the semiconductor surface include hydrogen, cadmium, gallium, and indium atoms and these can interact with gaseous Lewis base molecules like water, alcohols, ammonia, amines, sulfides, phosphines, ethers, ketones, and aldehydes.

A particularly strong interaction is complexation between hydrogen atoms and fluorine, oxygen, nitrogen, chlorine, or sulfur atoms. This is termed hydrogen bonding and is discussed on pages 268–272 of the aforementioned reference by Huheey. Hydrogen bonding can be anticipated for surfaces bearing O—H, S—H, or Se—H functional groups that are exposed to compounds like water, alcohols, ammonia and amines.

Reactions based on adduct formation or hydrogen bonding produce a change in the electric dipole moment of the surface. This will result in a change in the vertical charge distribution with respect to the radiation-emitting surface.

Neutral gaseous molecules useful in the practice of the present invention are given in Appendix E of Huheey supra. These compounds have the ability to bond to atoms on the reactive surface of the semiconductor.

Reactions of Vaska's complex. Taken from J. P. Collman and L. S. Hegedus, *Principles and Applications of Organotransition Metal Chemistry*, University Science Books: Mill Valley, Calif. (1980), p. 177.

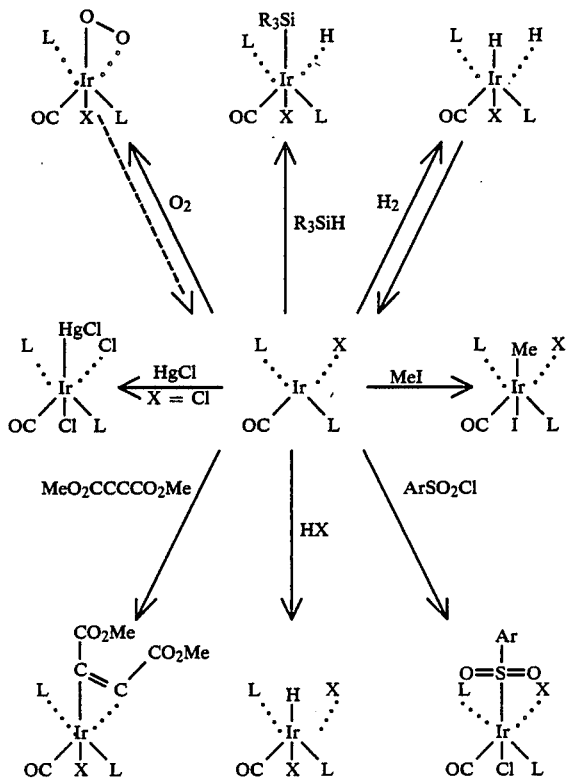

An oxidative addition is a reaction that formally increases the coordination number (the number of chemical moieties bonded to the metal) and oxidation state of the central metal. The resulting compound, an adduct, arises in many cases from cleavage of a chemical bond (e.g., M+X—Y→X—M—Y, where X—Y is oxidatively added to the metal complex, symbolized by M). A species like Vaska's complex can also form simple adducts with compounds like CO or $SO_2$ in which the coordination number increases without bond cleavage. The reverse reaction, reductive elimination, is a reaction that formally decreases the coordination number and oxidation state of the central metal. Furthermore, these reactions produce a change in the electric dipole moment of the molecule. If the molecule is coated onto the radiation-emitting surface, the oxidative addition/reductive elimination reaction will result in a change in the vertical charge distribution with respect to the radiation-emitting surface.

The complexes useful in the practice of the present invention are $d^8$ complexes and may be $d^8$ complexes of $Fe^0$, $Ru^0$, $Co^{+1}$, $Rh^{+1}$, $Ir^{+1}$, $Ni^{+2}$, $Pd^{+2}$, $Pt^{+2}$ and their congeners (members of the same family in the Periodic Table) which have a coordination number of 4 or 5. These complexes are described in *Inorganic Chemistry*, Keith F. Purcell, John C. Kotz, 1977 W. B. Saunders Co., Philadelphia, p. 939 and J. P. Collman et al., supra.

These complexes have at least one ligand which is capable of bonding or coordinating with a free metal or organic photoconductive surface or which ligand is substituted with a group having that ability. Typical end groups in such a ligand would be for example, in order of preference, silanes, epoxies, and acryloyl (including methacryloyl) groups.

Photoluminescent semiconductors are well known in the art. They are generally solid-state solutions of at least two or three elements which, when stimulated by actinic radiation, emit radiation. Both the actinic and emitted radiation are generally visible or near-visible the radiation-emitting surface radiation (300–900 nm). When of the semiconductor bonds to a gaseous compound that alters the electric field in the semiconductor surface, or the coating is a material which upon oxidative addition or reductive elimination alters the electric field in the semiconductor surface, the luminescence of the semiconductor has been found to be altered. Variations in photoluminescence are an indication of the presence of species that are involved in bonding to the radiation-emitting surface or in an oxidative addition/reductive elimination reaction with the coating.

Particularly useful n-type semiconductors that can be used to form the detectors according to the present invention are n-GaAs, n-GaAs$_x$P$_{1-x}$ (where x is from 0 to 1), n- and p-InP, CdS, CdSe, CdS$_x$Se$_{1-x}$ and graded CdS$_x$Se$_{1-x}$ ($0 \leq x \leq 1$). Other useful semiconductors would be ZnSe:Al, Cd$_x$Zn$_{1-x}$S ($0 \leq x \leq 1$), ZnS$_x$Se$_{1-x}$ $0 \leq X \leq 1$), and Cd$_x$Zn$_{1-x}$Se ($0 \leq x \leq 1$), and the like. The surface or compound that undergoes oxidative addition/reductive elimination or bonding reactions can be created on the elements according to standard manufacturing techniques.

A functional apparatus for actually using this phenomenon for detecting the presence of volatile species capable of adduct formation or hydrogen bonding to the semiconductor surface or oxidative addition/reductive elimination chemistry would have at least the following three components: the semiconductor (and optionally the coating), a source of actinic radiation directed at the radiation-emitting surface of the sensor or structure formed by the coating on the semiconductor, and an optical detector. In the case of the coated photoluminescent semiconductor, the sensor or structure is simply a piece of the semiconductor onto whose surface an analog of Vaska's complex has been chemically treated to yield the idealized structure as shown above; a number of representative compounds relevant to chemical sensing are also shown above. The actinic radiation source may be merely an opening exposing the sensor or structure to available light (room light, sunlight, etc.) or may be any internal source of radiation such as a light bulb, light emitting diode, or laser. The radiometer may be selected from amongst the many commercially available radiometers, its selection being primarily dependent upon the ultimate sensitivity desired in the final article. Fiber optics may be used to carry actinic radiation to the sensor or to carry emitted radiation away from the sensor.

Example 1

Samples of n-GaAs were prepared for derivatization by etching in 3:1 $HNO_3:HF$ at 50° C. for 30 seconds, rinsed in distilled water, immersed in 7M KOH at 50° C. for 30 minutes, rinsed in water, then acetone, and finally air-dried prior to derivatization. The samples prior to preparation were noted as n-GaAs:Te with carrier concentrations of $8 \times 10^{16}$ cm$-3$ and <100>orientation. Attachment proceeds by allowing the hydroxyl groups on the n-GaAs substrate to react with 2-(diphenylphosphino)ethyltriethoxysilane and with Vaska's complex, trans-ClIr(CO)[P(C$_6$H$_5$)$_3$], in a nitrogen-saturated, refluxing toluene solution.

When the sensor was illuminated with ultrabandgap light, the bandgap photoluminescence (PL) of the GaAs substrate (865 nm in the near IR) was sensitive to gaseous species capable of oxidative addition reactions. For example, several gases caused a substantial increase in the PL intensity: for oxygen, enhancements of up to 30% were observed; for hydrogen, up to 35%; for methyl iodide, up to 20%; and for sulfur dioxide, up to 100% enhancement was found. Moreover, in several instances, reductive elimination reactions could be exploited to reverse the effect on PL: exposure of the structure to nitrogen gas removed sulfur dioxide, hydrogen, and methyl iodide, for example, restoring the PL intensity to its original value. Independently confirmation by diffuse reflectance Fourier transform infrared spectroscopy showed that the chemistry of the reaction could be described in the following manner.

A chemical analog of Vaska's complex, covalently bonded through at least one and up to three of the three oxygen atoms to a photoconductive substrate (e.g., n-GaAs substrate), oxidatively adds a species XY (X—Y=H—H, O—O CH$_3$—I, e.g.) to yield an adduct; in many cases the reverse reaction, reductive elimination, can also be effected. The adduct changes the electric dipole moment, enabling photodetectable changes in an optically-coupled sensing device.

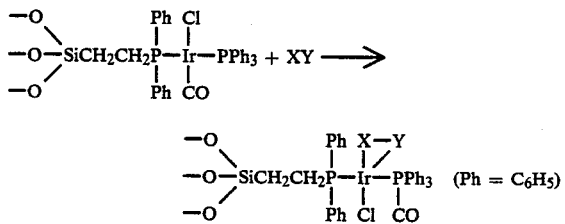

EXAMPLES 2-4

Example 1 was repeated except that the photoluminescent semiconductors used in the substrate were CdS, GaAs$_{0.7}$P$_{0.3}$, and CdS$_{0.9}$Se$_{0.1}$.

EXAMPLE 5

Example 1 was repeated except that 2-(diphenylphosphino)ethyltrichlorosilane was reacted with Vaska's complex. Similar results were obtained.

EXAMPLE 6

Samples of n-CdSe were prepared for use by etching in 30:1 $CH_3OH:Br_2$ at 20° C. for 30 seconds, rinsed in distilled water, immersed in $CH_3OH$ for 10 minutes in an ultrasonic cleaner, and finally air-dried. The samples prior to preparation were noted as undoped n-CdSe c-plates.

When the sensor was illuminated with ultrabandgap light, the bandgap photoluminescence (PL) of the CdSe substrate (720 nm in the near IR) was sensitive to gaseous species. For example, several gases caused a substantial decrease in the PL intensity relative to the PL intensity under nitrogen: for oxygen, loss of PL intensity of up to 20 % was observed and for sulfur dioxide, up to a 90% decrease was found. Other gases caused a substantial increase in the PL intensity: for ammonia, enhancements of up to 30% were observed; for water, up to a 300% enhancement was seen. Moreover, returning to a nitrogen atmosphere serves to reverse the effect on PL. Several gases like argon, methane, carbon monoxide, and carbon dioxide did not affect the PL intensity; these are gases that are not expected to form adducts or to hydrogen bond with the atoms comprising the semiconductor's surface.

For the interaction with sulfur dioxide, oxygen, and ammonia, the change in PL intensity varies with the excitation wavelength in accord with a dead-layer model. This model assumes that no PL originates from the nearsurface region of the semiconductor that supports the electric field. The good fit obtained to the model supports the notion that changes in the electric field in the semiconductor resulting from reactions occurring on the surface underlie the observed PL changes. Additionally, PL intensity was found to vary logarithmically with gas concentration, providing a working curve for this optically-coupled sensing device.

EXAMPLE 7

Example 6 was repeated except that the photoluminescent semiconductors used in the substrate were CdS and CdS$_{0.9}$Se$_{0.1}$. The experiment was also repeated with n-InP, undoped n-GaAs, and photoelectrochemically etched n-CdSe as substrates and sulfur dioxide as the reacting gas.

As noted in the above description of the invention and the examples, the photoluminescent substrates useful in the present invention are either uncoated surfaces or surfaces having compounds reacted thereto which are capable of undergoing adduct formation or hydrogen bonding to produce a change in the electric dipole moment of the surface.

What is claimed is:

1. An apparatus for detecting the presence of chemical compounds comprising:
    (a) a photoluminescent semiconductor having a radiation emitting surface and having a reacted material bonded to said radiation-emitting surface of said semiconductor, said reacted material being capable of undergoing an oxidative addition/reductive elimination reaction with volatile compounds to produce a reaction product bonded to said radiation-emitting surface, said reacted material having an electrical charge distribution which is vertical with respect to the radiation-emitting surface, and said reaction product altering the vertical charge distribution with respect to the radiation-emitting surface, said charge distribution being capable of altering an electric field in said semiconductor, (b) a source of actinic radiation that can impinge on said radiation-emitting surface of the semiconductor, and (c) a means for detecting changes in the radiation emitted from said radiation-emitting surface.

2. The apparatus of claim 1 wherein said reactive material comprises a $d^8$ complex.

3. The apparatus of claim 1 wherein said reactive material comprises a $d^8$ complex of $Fe^0$, $Ru^0$, $Co^{+1}$, $Rh^{+1}$, $Ir^{+1}$, $Ni^{+2}$, $Pd^{+2}$, $Pt^{+2}$ or their congeners.

4. The apparatus of claim 1 wherein said source of actinic radiation comprises visible light.

5. The apparatus of claim 4 wherein said reactive material comprises a $d^8$ complex.

6. The apparatus of claim 1 wherein said semiconductor comprises a solid-state solution of at least two elements selected from the group consisting of (a) cadmium, selenium, and sulfur, (b) zinc, selenium, and sulfur, (c) cadmium, zinc, and selenium, (d) cadmium, zinc, and sulfur, (e) cadmium and selenium, (f) cadmium and sulfur, (g) zinc and selenium doped with aluminum, (h) gallium and arsenic, (i) allium, arsenic, and phosphorus, and (j) gallium and phosphorus, and (k) indium and phosphorus.

7. The apparatus of claim 6 wherein said means for detecting changes in the characteristics of the radiation is a radiometer.

8. The apparatus of claim 6 wherein said semiconductor has a coating of said reactive material containing Vaska's complex or a derivative thereof that can undergo oxidative addition/reductive elimination reactions.

9. The apparatus of claim 6 wherein said reactive material comprises a $d^8$ complex.

10. The apparatus of claim 1 wherein said means for detecting changes in the characteristics of the radiation is a radiometer.

11. The apparatus of claim 10 wherein said source of actinic radiation comprises visible light.

12. The apparatus of claim 10 wherein said reactive material comprises a $d^8$ complex.

13. The apparatus of claim 10 wherein said reactive material comprises a $d^8$ complex of $Fe^0$, $Ru^0$, $Co^{+1}$, $Rh^{+1}$, $Ir^{+1}$, $Ni^{+2}$, $Pd^{+2}$, $Pt^{+2}$ or their congeners.

14. The apparatus of claim 10 wherein said semiconductor has a coating of said reactive material containing Vaska's complex or a derivative thereof that can undergo oxidative addition/reductive elimination reactions.

15. The apparatus of claim 14 wherein said source of actinic radiation comprises visible light.

16. The process for detecting the presence of chemical components comprising providing a photoluminescent semiconductor having at least one radiation-emitting surface having a reacted material bonded to said radiation-emitting surface, said reacted material being capable of undergoing an oxidative addition/reductive elimination reaction with volatile compounds to produce an adduct or reduct which will alter the vertical charge distribution with respect to the radiation-emitting surface, said charge distribution being capable of altering an electric field in said semiconductor, irradiating said semiconductor with actinic radiation, observing the characteristics of radiation emitted from said semiconductor, then exposing said surface to an environment having chemical compounds capable of reacting with said reacted material by oxidative addition/reductive elimination reactions and detecting any changes in the radiation emitted from said surface.

17. The process of claim 16 wherein said actinic radiation is ambient light.

18. The process of claim 16 wherein light from a light bulb, laser, or light emitting diode provides said actinic radiation.

19. An apparatus for detecting the presence of chemical compounds comprising:

(a) a photoluminescent semiconductor having a reacted material on a radiation emitting surface thereof, said reacted material bonding to various gases through adduct formation or hydrogen bonding to produce a product bonded to said radiation-emitting surface, said reacted material having an electrical charge distribution which is vertical with respect to the radiation-emitting surface, and said product altering the vertical charge distribution with respect to the radiation-emitting surface, said charge distribution being capable of altering an electric field in said semiconductor, (b) a source of actinic radiation that can impinge on said radiation-emitting surface of the semiconductor, and (c) a means for detecting changes in the radiation emitting from said radiation-emitting surface.

20. The process of detecting the presence of chemical components comprising providing a photoluminescent semiconductor having at least one radiation-emitting surface, said surface being capable of bonding with volatile compounds to produce an adduct or reduct which will alter the vertical charge distribution with respect to the radiation-emitting surface, said charge distribution being capable of altering the electric field in said semiconductor, irradiating said semiconductor with actinic radiation, observing the characteristics of radiation emitted from said semiconductor, then exposing said surface to an environment having chemical compounds capable of bonding with said surface by adduct formation or hydrogen bonding and detecting any changes in the characteristics of radiation emitted from said surface.

* * * * *

UNITED STATES PATENT AND TRADEMARK OFFICE
CERTIFICATE OF CORRECTION

PATENT NO. : 4,752,588
DATED : June 21, 1988
INVENTOR(S) : Ellis, Meyer and Lisensky It is certified that error appears in the above-identified patent and that said Letters Patent is hereby corrected as shown below:

Column 5, line 9 "Example 1" should be --EXAMPLE 1-- and centered on column.

Column 5, line 16 "cm-3" should be --$cm^{-3}$--.

Column 5, line 20 "[$P(C_6H_5)_3$] should be --[$P(C_6H_5)_3]_2$--.

Signed and Sealed this

Twenty-fourth Day of October, 1989

Attest:

DONALD J. QUIGG

*Attesting Officer*

*Commissioner of Patents and Trademarks*

UNITED STATES PATENT AND TRADEMARK OFFICE
CERTIFICATE OF CORRECTION

PATENT NO. : 4,752,588
DATED : June 21, 1988
INVENTOR(S) : Arthur B. Ellis, et. al.

It is certified that error appears in the above-indentified patent and that said Letters Patent is hereby corrected as shown below:

Column 1, line 3, under Title: This invention was made with Government support under Contract N00014-85-K-0631 awarded by the Department of the Navy. The Government has certain rights in the invention.

Signed and Sealed this

Thirty-first Day of August, 1993

*Attest:*

BRUCE LEHMAN

*Attesting Officer*  *Commissioner of Patents and Trademarks*